March 11, 1958 E. A. MANDA, JR Plant Pat. 1,687
ROSE PLANT
Filed July 29, 1957
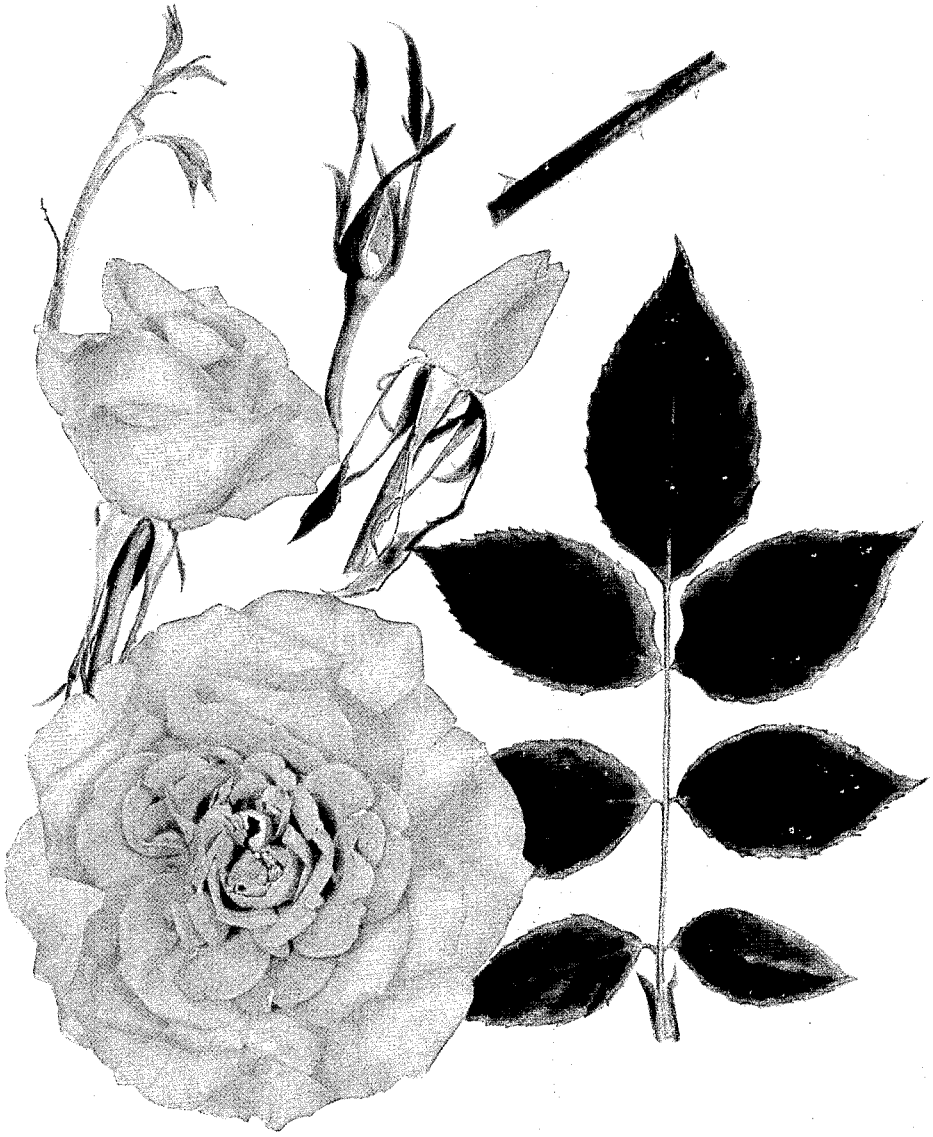
Inventor.
Edward A. Manda, Jr.
By: Robb & Robb
Attorneys.

United States Patent Office

Plant Pat. 1,687
Patented Mar. 11, 1958

1,687

ROSE PLANT

Edward A. Manda, Jr., Pleasant Hills, Mo., assignor to Jackson & Perkins Company, Newark, N. Y., a corporation of New York Application July 29, 1957, Serial No. 674,988

1 Claim. (Cl. 47—61)

The present invention relates to a new and distinct variety of rose plant of the hybrid tea class, which was discovered by me as a sport of the variety "Better Times" (Plant Patent No. 23).

The new variety was discovered by me in the benches of my greenhouses at Pleasant Hill, Missouri, where plants of the variety "Better Times" were being grown by me. At the time of my discovery, my attention was attracted thereto by the fact that one plant among the regular bench plants aforementioned exhibited a flower color which was different from that of "Better Times," more numerous flower petals, more vigorous habit of plant growth and darker foliage than is characteristic of the variety "Better Times." Upon closer observation, I found that the plant to which my attention had been attracted had sported, and I thereupon took steps to preserve the same, keep it under observation, and to later asexually reproduce the sport. These observations and asexual reproductions, as performed by grafting on Manetti, at Pleasant Hill, Missouri, conclusively established that the aforementioned characteristics were fixed and established and capable of being transmitted through succeeding propagations.

Except for the new characteristics described in the foregoing, the sport otherwise generally corresponds to its parent variety, but it is definitely distinguished therefrom, as well as from all other varieties of its class of which I am aware.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Sport of "Better Times."
Classification:
*Botanic.*—Hybrid tea.
*Commercial.*—Hybrid tea.

*Flower*

(Observations made from specimens grown in a greenhouse at Newark, New York, in the late morning and in the latter part of January.)

Blooming habit: Recurrent—continuous.
Bud:
*Size.*—Large.
*Form.*—Pointed; is not affected by wet or hot weather.
*Color.*—When sepals first divide—Pomegranate Purple, Plate 12. When petals begin to unfurl—Pomegranate Purple, Plate 12, lightly overcast with Rose Red, Plate 12. When half-blown: inside of petals—Carmine, Plate 1; reverse of petals—Rose Red, Plate 12, lightly overcast with Pomegranate Purple, Plate 12.
*Sepals.*—Branched; with "hood" above bud; curl back when petals begin to unfurl. Color: inside—Light Fluorite Green, Plate 32; outside—Spinach Green, Plate 5.
*Calyx.* — Color — Light Bice Green, Plate 17. Shape — pear. Size — small. Aspect—smooth. Odor when rubbed—none.
*Peduncle.* — Length — long. Aspect — smooth, Strength — erect; heavy. Color — Rinnemann's Green, Plate 18.
*Opening.*—Opens up well; is not affected by adverse weather conditions.

Bloom:
*Size.*—Large. Average size when fully expanded—from 4½ to 5 inches.
*Borne.*—Both singly and several together.
*Stems.*—Long; strong.
*Form (when first open).*—High-centered. Permanence—retains its form to the end.
*Petalage.*—Double (full but open center). Number of petals under normal conditions—from 35 to 45.
*Color.*—Center of flower—Carmine, Plate 1, lightly overcast with Spectrum Red, Plate 1. Outer petals—Carmine, Plate 1, lightly overcast with Rose Red, Plate 12. Base of petals (aiglet)—Citron Yellow, Plate 14. Inside of petals—Carmine, Plate 1, lightly overcast with Pomegranate Purple, Plate 12. Reverse of petals—Pomegranate Purple, Plate 12, lightly overcast with Tyrian Rose, Plate 12. General tonality from a distance—Carmine, Plate 1.
*Discoloration.*—General tonality at the end of first day—Carmine, Plate 1. Second day—Carmine, Plate 1. Third day—Carmine, Plate 1, lightly overcast with Rose Red, Plate 12.

Petals:
*Texture.*—Leathery; is not affected by hot or wet weather.
*Appearance.* — Inside — velvety. Outside — Satiny.
*Form.*—Oval; slightly notched.
*Arrangement.* — Imbricated (regularly arranged shingle-like).
*Petaloids in center.*—Few; small.
*Persistence.*—Drop off cleanly.
*Fragrance.*—Strong. Nature—"Old Rose perfume" (centifolia).
*Lasting quality.*—On the plant—very long. As cut flower—very long.

*Genital organs*

Stamens, anthers: Medium size; many; regularly arranged around styles. Color—Antimony Yellow, Plate 15.
Stamens, filaments (threads): Medium length. Color—Begonia Rose, Plate 1.
Pollen: Color—Cartridge Buff, Plate 30.
Styles: Gunched; uneven length; medium length; thin.
Stigmas: Color—Cream Buff, Plate 30.
Ovaries: All enclosed in calyx.
Hips: None.
Seeds: None.

*Plant*

Form: *Bush.*
Growth: Vigorous; upright.
Foliage: Compound of 5 to 7 leaflets.
*Size.*—Large.
*Quantity.*—Abundant.
*Color.*—New foligae: upper side—Eugenia Red, Plate 13; under side—Eugenia Red, Plate 13, with center vein Parrot Green, Plate 6. Old foligae: upper side—Varley's Green, Plate 18; under side—Light Hellebore Green, Plate 17.

*Shape.*—Oval pointed.

*Texture.* — Upper side—leathery. Under side—smooth.

*Ribs and veins.*—Ordinary.

*Edge.*—Serrated (sawtoothed).

*Serration.*—Both double and single; sharp.

*Leaf stem.*—Color—Rainette Green, Plate 31. Under side—smooth.

*Stipules.*—Long; smooth.

Wood:

*New wood.*—Color—Yellowish Oil Green, Plate 5. Bark—smooth.

*Old wood.*—Color—Cress Green, Plate 31. Bark—smooth.

Thorns:

*Thorns.*—Quantity: on main stalks from base—few; on laterals from stalk—few. Form—narrow base; short; hooked downward. Color (when young)—Old Rose, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by its general similarity to its parent variety "Better Times" (Plant Patent No. 23), but being essentially distinguished therefrom by its more vigorous habit of growth, darker foliage, greater flower petalage, and the distinctive Carmine general color tonality, lightly overcast with Spectrum Red, of its flowers.

No references cited.